(12) United States Patent
Hejazi

(10) Patent No.: US 11,602,164 B2
(45) Date of Patent: Mar. 14, 2023

(54) AEROSOL DELIVERY DEVICE WITH GRADED POROSITY FROM INNER TO OUTER WALL SURFACES

(71) Applicant: RAI Strategic Holdings, Inc., Winston-Salem, NC (US)

(72) Inventor: Vahid Hejazi, Concord, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 447 days.

(21) Appl. No.: 16/353,556

(22) Filed: Mar. 14, 2019

(65) Prior Publication Data

US 2020/0288787 A1    Sep. 17, 2020

(51) Int. Cl.
  *A24F 7/00*    (2006.01)
  *A24D 1/14*    (2006.01)
  *A61M 11/04*   (2006.01)

(52) U.S. Cl.
  CPC .................. *A24F 7/00* (2013.01); *A24D 1/14* (2013.01); *A61M 11/042* (2014.02)

(58) Field of Classification Search
  None
  See application file for complete search history.

(56) References Cited

U.S. PATENT DOCUMENTS

| 2,057,353 | A | 10/1936 | Whittemore, Jr. |
| 2,104,266 | A | 1/1938 | McCormick |
| 3,200,819 | A | 8/1965 | Gilbert |
| 4,922,901 | A | 5/1990 | Brooks et al. |
| 5,060,671 | A | 10/1991 | Counts et al. |
| 5,093,894 | A | 3/1992 | Deevi et al. |
| 5,261,424 | A | 11/1993 | Sprinkel, Jr. |
| 5,388,574 | A | 2/1995 | Ingebrethsen et al. |
| 5,530,225 | A | 6/1996 | Hajaligol |
| 5,687,746 | A | 11/1997 | Rose et al. |
| 5,726,421 | A | 3/1998 | Fleischhauer et al. |

(Continued)

FOREIGN PATENT DOCUMENTS

| CN | 1541577 | 11/2004 |
| CN | 2719043 | 8/2005 |

(Continued)

*Primary Examiner* — Joseph S Del Sole
*Assistant Examiner* — Guy F Mongelli
(74) *Attorney, Agent, or Firm* — Womble Bond Dickinson (US) LLP

(57) ABSTRACT

The present disclosure relates to a flavor delivery article, a mouthpiece, a cartridge, and/or an aerosol delivery device that includes such flavor delivery article. The flavor delivery article includes a hollow elongate unit formed of a substantially continuous wall extending between a first end and a second end and defining an interior storage volume, the substantially continuous wall being formed of a porous material having a graded porosity across a thickness of the substantially continuous wall. The flavor delivery article further includes a flavor liquid contained with the interior storage volume of the hollow elongate unit. The flavor delivery article may be positioned anywhere within an aerosol delivery device (or a mouthpiece or a cartridge of an aerosol delivery device) wherein the flavor liquid may pass through the substantially continuous wall to be entrained in an air stream and/or vapor stream and/or aerosol stream passing through the aerosol delivery device.

27 Claims, 11 Drawing Sheets

(56) References Cited

U.S. PATENT DOCUMENTS

| | | | |
|---|---|---|---|
| 5,865,185 A | 2/1999 | Collins et al. | |
| 5,894,841 A | 4/1999 | Voges | |
| 6,125,853 A | 10/2000 | Susa et al. | |
| 6,155,268 A | 12/2000 | Takeuchi | |
| 7,117,867 B2 | 10/2006 | Cox et al. | |
| 7,832,410 B2 | 11/2010 | Hon | |
| 8,314,591 B2 | 11/2012 | Terry et al. | |
| 8,365,742 B2 | 2/2013 | Hon | |
| 8,499,766 B1 | 8/2013 | Newton | |
| 2003/0089370 A1* | 5/2003 | Daffer | A61H 35/00 128/201.24 |
| 2003/0154991 A1* | 8/2003 | Fournier | A24F 40/50 131/194 |
| 2004/0159327 A1* | 8/2004 | Dante | A24D 1/00 131/337 |
| 2005/0016550 A1 | 1/2005 | Katase | |
| 2006/0196518 A1 | 9/2006 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0188490 A1 | 7/2009 | Hon | |
| 2009/0272379 A1 | 11/2009 | Thorens et al. | |
| 2009/0293893 A1* | 12/2009 | Mishra | B01D 69/082 131/332 |
| 2010/0163062 A1* | 7/2010 | Atchley | A24B 13/00 131/119 |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0290248 A1 | 12/2011 | Schennum | |
| 2012/0111347 A1 | 5/2012 | Hon | |
| 2012/0260927 A1 | 10/2012 | Liu | |
| 2012/0279512 A1 | 11/2012 | Hon | |
| 2013/0037041 A1 | 2/2013 | Worm et al. | |
| 2013/0056013 A1 | 3/2013 | Terry et al. | |
| 2013/0087160 A1* | 4/2013 | Gherghe | A24F 40/90 131/329 |
| 2013/0167854 A1* | 7/2013 | Shin | A61M 15/06 131/329 |
| 2013/0306084 A1 | 11/2013 | Flick | |
| 2014/0000638 A1 | 1/2014 | Sebastian et al. | |
| 2014/0014106 A1* | 1/2014 | Smutney | A61M 15/0028 128/203.15 |
| 2014/0060554 A1 | 3/2014 | Collett et al. | |
| 2014/0060555 A1 | 3/2014 | Chang et al. | |
| 2014/0096781 A1 | 4/2014 | Sears et al. | |
| 2014/0096782 A1 | 4/2014 | Ampolini et al. | |
| 2014/0166029 A1 | 6/2014 | Weigensberg et al. | |
| 2014/0209105 A1 | 7/2014 | Sears et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2015/0101606 A1* | 4/2015 | White | A61M 15/00 131/194 |
| 2015/0181937 A1* | 7/2015 | Dubief | A24F 40/46 131/329 |
| 2015/0208728 A1* | 7/2015 | Lord | A24F 7/00 131/329 |
| 2015/0216237 A1* | 8/2015 | Wensley | A24F 40/46 131/273 |
| 2015/0335070 A1* | 11/2015 | Sears | A24F 40/42 131/328 |
| 2015/0335073 A1* | 11/2015 | Li | A24F 40/44 131/329 |
| 2016/0050975 A1* | 2/2016 | Worm | A24F 40/95 131/328 |
| 2016/0135506 A1 | 5/2016 | Sanchez et al. | |
| 2016/0331030 A1* | 11/2016 | Ampolini | A24F 40/70 |
| 2016/0366947 A1* | 12/2016 | Monsees | A24F 40/42 |
| 2017/0340003 A1* | 11/2017 | Batista | A24B 15/167 |
| 2017/0367411 A1 | 12/2017 | Duc | |
| 2018/0084830 A1* | 3/2018 | Xu | A24F 40/42 |
| 2019/0045837 A1* | 2/2019 | Spencer | H05B 1/0297 |
| 2019/0254344 A1 | 8/2019 | Hepworth et al. | |
| 2019/0274358 A1* | 9/2019 | Reevell | A24D 1/20 |
| 2020/0187561 A1 | 6/2020 | Sudlow et al. | |

FOREIGN PATENT DOCUMENTS

| | | |
|---|---|---|
| CN | 201379072 | 1/2010 |
| CN | 207969655 | 10/2018 |
| CN | 208338878 | 1/2019 |
| EP | 0 295 122 | 12/1988 |
| EP | 0 845 220 | 6/1998 |
| EP | 1 618 803 | 1/2006 |
| GB | 2469850 | 11/2010 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | WO 2018/114312 | 6/2018 |

\* cited by examiner

AEROSOL DELIVERY DEVICE WITH GRADED POROSITY FROM INNER TO OUTER WALL SURFACES

FIELD OF THE DISCLOSURE

The present disclosure relates to aerosol delivery devices, and more particularly to an aerosol delivery device that include a reservoir and a vaporizing assembly, which may utilize electrical power to heat an aerosol precursor composition for the production of an aerosol. The aerosol precursor composition, which may incorporate materials and/or components that may be made or derived from tobacco or otherwise incorporate tobacco, is heated by the vaporizing assembly to produce an inhalable substance for human consumption.

BACKGROUND

Many smoking articles have been proposed through the years as improvements upon, or alternatives to, smoking products based upon combusting tobacco. Exemplary alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference.

The goal of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Lorillard Technologies, Inc.; COHITA™, COLIBRI™, ELITE CLASSIC™, MAGNUM™, PHANTOM™and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™, JET™, MAXXQ™, PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™.

Certain existing embodiments of aerosol delivery devices include a control body (i.e., a power source assembly) and a cartridge (i.e., a reservoir housing). A power source (e.g., a battery) may be positioned in the control body, and an aerosol precursor composition may be retained and/or stored within the cartridge. It would be desirable to provide a cartridge capable of adding one or more flavor additives to the aerosol precursor composition as desired by the user.

SUMMARY OF THE DISCLOSURE

In various embodiments, the present disclosure provides a flavor delivery article that can be included in, or combined with, an aerosol delivery device. The flavor delivery article can incorporate defined porosity gradients that allow an internally stored flavor liquid to migrate outwardly therefrom to an outer surface of the flavor delivery article for entrainment in a gaseous stream. As such, the flavor delivery article is configured for inclusion within or attachment to an aerosol delivery device in any location therein where a flowing gaseous stream may pass therealong.

The present disclosure can provide a variety of articles that are each adapted to or configured to provide a flavor. In some embodiments, the disclosure can relate to a flavor delivery article that can be adapted to or configured to be combined with a further article, such as a cartridge of an aerosol delivery device and/or a mouthpiece that is attachable to a cartridge of an aerosol delivery device. In further embodiments, the disclosure can relate to a flavor delivery mouthpiece that includes a flavor delivery article and that is adapted to or configured to be attached to a cartridge of an aerosol delivery device. In other embodiments, the present disclosure can relate to a cartridge of an aerosol delivery device. Such cartridge can include a flavor delivery article that can be included directly into the cartridge housing and/or can be include in a mouthpiece that is attached to the cartridge housing. In still further embodiments, the present disclosure can relate to an aerosol delivery device that includes a power unit and a cartridge. The power unit and cartridge can be provided in a single housing or can be provided in separate housings. The aerosol delivery device in particular can include a flavor delivery article combined therewith, such as being included in the cartridge and/or being included in a mouthpiece that is attached to the cartridge.

In an example embodiment, a flavor delivery article according to the present disclosure can comprise: a hollow elongate unit formed of a substantially continuous wall extending between a first end and a second end and defining an interior storage volume, the substantially continuous wall being formed of a porous material having a graded porosity across a thickness of the substantially continuous wall; and a flavor liquid contained with the interior storage volume of the hollow elongate unit. In further embodiments, the flavor delivery article can be further defined in relation to any one or more of the following statements, which statements can be combined in any order and number.

The porous material forming the substantially continuous wall of the hollow elongate unit can be a polymeric material.

The polymeric material can be selected from the group consisting of polyethersulfone, polypropylene, polyethylene, polyester, nylon, cellulose nitrate, regenerated cellulose, cellulose acetate, and combinations thereof.

The porous material forming the substantially continuous wall of the hollow elongate unit can be a ceramic material.

The graded porosity can be configured such that an average size of pores in the substantially continuous wall of the hollow elongate unit increases across the thickness of the substantially continuous wall from an interior surface to an exterior surface of the outer wall.

The pores in the substantially continuous wall of the hollow elongate unit can have a first average size at one of the interior surface and the exterior surface of about 10 nm to about 3 μm.

The pores in the substantially continuous wall of the hollow elongate unit can have a second average size at an other of the interior surface and the exterior surface of about 0.5 μm to about 30 μm.

One or both of the first end and the second end of the hollow elongate unit can be open.

The flavor delivery article further can comprise an end unit engaging one or both of the first end and the second end of the hollow elongate unit.

The end unit can be a lattice structure comprising a plurality of airflow passages therethrough.

The flavor delivery article further can comprise an outer casing.

In an example embodiment, the present disclosure can provide a flavor delivery mouthpiece that comprises: a flavor delivery article as otherwise described herein that is positioned within a mouthpiece shell that includes a first end and an opposing, second end, the second end including one or more apertures adapted for passage of air therethrough, wherein the flavor delivery article positioned within the mouthpiece shell is spaced apart from an interior surface of the mouthpiece shell so as to allow passage of the air through the mouthpiece shell between the flavor delivery article and the interior surface of the mouthpiece shell. In further embodiments, the flavor delivery mouthpiece can be further defined in relation to any one or more of the following statements, which statements can be combined in any order and number The mouthpiece shell can comprise one or more protrusions extending inwardly from the interior surface of the mouthpiece shell.

The one or more protrusions can be adapted to contact with flavor delivery article and substantially maintain a lateral position of the flavor delivery article within the mouthpiece shell.

The flavor delivery mouthpiece further can comprise a mandrel positioned within the mouthpiece shell proximate to the second end thereof, the mandrel being adapted to engage one of the first end and the second end of the hollow elongate unit of the flavor delivery article.

The flavor delivery mouthpiece further can comprise a removably replaceable cover adapted to engage the second end of the mouthpiece shell.

In an example embodiment, the present disclosure can provide a cartridge for an aerosol delivery device, the cartridge comprising: a cartridge housing having a mouthend; a reservoir including an aerosol precursor composition; a heater adapted to vaporize the aerosol precursor composition; and a flavor delivery mouthpiece as otherwise described herein that is engaged with the cartridge such that the first end of the mouthpiece shell is attached to the mouthend of the cartridge housing. In further embodiments, the cartridge can be further defined in relation to any one or more of the following statements, which statements can be combined in any order and number The cartridge further can comprise a liquid transport element configured for transport of the aerosol precursor composition between a reservoir and the heater.

The reservoir can include a fibrous material.

The reservoir can be a tank.

In an example embodiment, the present disclosure can provide an aerosol delivery device comprising: a power unit housing including a power source and a controller; and a cartridge as otherwise described herein.

In an example embodiment, the present disclosure can provide a cartridge for an aerosol delivery device, the cartridge comprising: a cartridge housing having a mouthend; a reservoir including an aerosol precursor composition; a heater adapted to vaporize the aerosol precursor composition; and a flavor delivery article comprising: a hollow elongate unit formed of a substantially continuous wall extending between a first end and a second end and defining an interior storage volume, the substantially continuous wall being formed of a porous material having a graded porosity across a thickness of the substantially continuous wall; and a flavor liquid contained with the interior storage volume of the hollow elongate unit. In further embodiments, the cartridge can be further defined in relation to any one or more of the following statements, which statements can be combined in any order and number The cartridge further can comprise an air entry and an airflow passage through the cartridge.

The heater and the flavor delivery article can be both positioned substantially within the airflow passage.

The flavor delivery article can be positioned in the airflow passage upstream from the heater.

The flavor delivery article can be positioned in the airflow passage downstream from the heater.

The flavor delivery article can be positioned in a mouthpiece attached to the mouthend of the cartridge housing.

BRIEF DESCRIPTION OF THE FIGURES

In order to assist the understanding of aspects of the disclosure, reference will now be made to the appended drawings, which are not necessarily drawn to scale and in which like reference numerals refer to like elements. The drawings are exemplary only, and should not be construed as limiting the disclosure.

DETAILED DESCRIPTION

Figure 1:
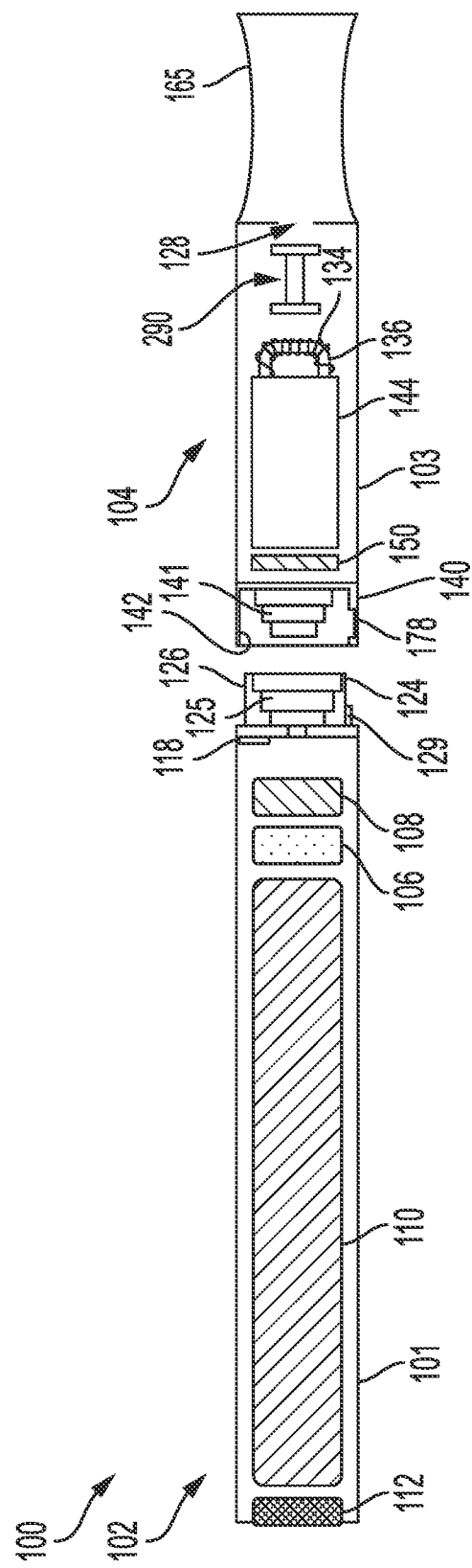
FIG. 1 illustrates a partial cross-sectional view of an example embodiment of an aerosol delivery device according to embodiments of the present disclosure.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The present disclosure provides descriptions of aerosol delivery devices. The aerosol delivery devices may use electrical energy to heat a material to form an inhalable substance; such articles may be sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device may yield vapors (including vapors within aerosols that can be considered to be visible aerosols that might be considered to be described as smoke-like) resulting from volatilization or vaporization of certain components of the article or device, although in other implementations the aerosol may not be visible. In some implementations, aerosol delivery devices may incorporate tobacco and/or components derived from tobacco. As such, the aerosol delivery device can be characterized as an electronic smoking article such as an electronic cigarette or "e-cigarette."

While the systems are generally described herein in terms of implementations associated with aerosol delivery devices such as so-called "e-cigarettes," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other embodiments (e.g., rectangular or fob-shaped). Thus, an aerosol delivery device as described herein may take on any configuration desired.

In one implementation, all of the components of the aerosol delivery device are contained within one outer body, which may be defined as a housing or shell. Alternatively, an aerosol delivery device can comprise two or more shells that are joined and are separable. For example, an aerosol delivery device can comprise a control body or power unit including a shell containing one or more reusable components (e.g., a rechargeable battery and various electronics for controlling the operation of that article), and also can comprise a removably attached shell configured as a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure may comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance or inductive heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined air flow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (which may itself contain one or more flavorants, medicaments, or other additives) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery and/or other electrical power source (e.g., a capacitor) to provide current flow sufficient to provide various functionalities to the aerosol delivery device, such as powering of a heater, powering of control systems, powering of indicators, and the like. The power source can take on various implementations. In one example, the power source is able to deliver sufficient power to rapidly heat the heating element to provide for aerosol formation and power the aerosol delivery device through use for a desired duration of time. The power source may be sized to fit conveniently within the aerosol delivery device so that the aerosol delivery device can be easily handled. Additionally, in one embodiment, a power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure as well as manufacturers, designers, and/or assignees of components and related technologies that may be employed in the aerosol delivery device of the present disclosure are described in U.S. patent application Ser. No. 15/222,615, filed Jul. 28, 2016, to Watson et al., which is incorporated herein by reference in its entirety.

One example embodiment of an aerosol delivery device 100 illustrating components that may be utilized in an aerosol delivery device according to the present disclosure is provided in FIG. 1. As seen in the cut-away view illustrated therein, the aerosol delivery device 100 can comprise a power unit 102 and a cartridge 104 that can be permanently or detachably aligned in a functioning relationship. Engagement of the power unit 102 and the cartridge 104 can be press fit (as illustrated), threaded, interference fit, magnetic, or the like. In particular, connection components, such as further described herein may be used. For example, the power unit may include a coupler that is adapted to engage a connector on the cartridge.

In specific embodiments, one or both of the power unit 102 and the cartridge 104 may be referred to as being disposable or as being reusable. For example, the power unit may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a power unit connector at an opposing end is disclosed in U.S. Pat. Pub. No. 2014/0261495 to Novak et al., which is incorporated herein by reference in its entirety. Further, in some embodiments the cartridge may comprise a single-use cartridge, as disclosed in U.S. Pat. No. 8,910,639 to Chang et al., which is incorporated herein by reference in its entirety.

As illustrated in FIG. 1, a power unit 102 can be formed of a power unit shell 101 that can include a control component 106 (e.g., a printed circuit board (PCB), an integrated circuit, a memory component, a microcontroller, or the like), a flow sensor 108, a battery 110, and an LED 112, and such components can be variably aligned. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference.

A cartridge 104 can be formed of a cartridge shell 103 enclosing the reservoir 144 that is in fluid communication with a liquid transport element 136 adapted to wick or otherwise transport an aerosol precursor composition stored in the reservoir housing to a heater 134. A liquid transport element can be formed of one or more materials configured for transport of a liquid, such as by capillary action. A liquid transport element can be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element thus can be any material that contains an open pore network (i.e., a plurality of pores that are interconnected so that fluid may flow from one pore to another in a plurality of direction through the element).

Various embodiments of materials configured to produce heat when electrical current is applied therethrough may be employed to form the resistive heating element 134. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, graphite and graphite-based materials (e.g., carbon-based foams and yarns) and ceramics (e.g., positive or negative temperature coefficient ceramics). Various other implementations of a heating element likewise may be employed. For example, a metal mesh may be positioned around a cylindrical wick, or a ribbon-like metal mesh may be positioned on a ribbon-shaped or sheet-shaped wick. For example, a heating element may be configured to heat the aerosol precursor composition disposed within a liquid transport element via radiant heating, as described in U.S. Pat. App. Pub. No. 2017/0020193, filed Dec. 3, 2015, the content of which is incorporated herein by reference. In another implementation, the heating element may be configured to heat the aerosol precursor composition via inductive heating, as described in U.S. Pat. App. Pub. No. 2017/0127722, filed Nov. 6, 2015, the content of which is incorporated herein by reference. A variety of heater components may be used in the present aerosol delivery device. In various implementations, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference.

An opening 128 may be present in the cartridge shell 103 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include one or more electronic components 150, which may include an integrated circuit, a memory component, a sensor, or the like. The electronic component 150 may be adapted to communicate with the control component 106 and/or with an external device by wired or wireless means. The electronic component 150 may be positioned anywhere within the cartridge 104 or its base 140.

Although the control component 106 and the flow sensor 108 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the power unit. In some embodiments, the air flow sensor may comprise its own circuit board or other base element to which it can be attached. In some embodiments, a flexible circuit board may be utilized. A flexible circuit board may be configured into a variety of shapes, include substantially tubular shapes.

The power unit 102 and the cartridge 104 may include components adapted to facilitate a fluid engagement therebetween. As illustrated in FIG. 1, the power unit 102 can include a coupler 124 having a cavity 125 therein. The cartridge 104 can include a base 140 adapted to engage the coupler 124 and can include a projection 141 adapted to fit within the cavity 125. Such engagement can facilitate a stable connection between the power unit 102 and the cartridge 104 as well as establish an electrical connection between the battery 110 and control component 106 in the power unit and the heater 134 in the cartridge. Further, the power unit shell 101 can include an air entry 118, which may be a notch in the shell where it connects to the coupler 124 that allows for passage of ambient air around the coupler and into the shell where it then passes through the cavity 125 of the coupler and into the cartridge through the projection 141.

A coupler and a base useful according to the present disclosure are described in U.S. Pat. Pub. No. 2014/0261495 to Novak et al., the disclosure of which is incorporated herein by reference in its entirety. For example, a coupler as seen in FIG. 1 may define an outer periphery 126 configured to mate with an inner periphery 142 of the base 140. In one embodiment the inner periphery of the base may define a radius that is substantially equal to, or slightly greater than, a radius of the outer periphery of the coupler. Further, the coupler 124 may define one or more protrusions 129 at the outer periphery 126 configured to engage one or more recesses 178 defined at the inner periphery of the base. However, various other embodiments of structures, shapes, and components may be employed to couple the base to the coupler. In some embodiments the connection between the base 140 of the cartridge 104 and the coupler 124 of the power unit 102 may be substantially permanent, whereas in other embodiments the connection therebetween may be releasable such that, for example, the power unit may be reused with one or more additional cartridges that may be disposable and/or refillable.

The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, multifaceted shapes, or the like. In particular, the power unit 102 may be non-rod-like and may rather be substantially rectangular, round, or have some further shape. Likewise, the power unit 102 may be substantially larger than a power unit that would be expected to be substantially the size of a conventional cigarette.

The reservoir 144 illustrated in FIG. 1 can be a container (e.g., formed of walls substantially impermeable to the aerosol precursor composition) or can be a fibrous reservoir. Container walls can be flexible and can be collapsible. Container walls alternatively can be substantially rigid. A container reservoir may be referred to as a tank. Moreover, a fibrous material may be provided in at least a portion of a container. In exemplary embodiments, the reservoir 144 can comprise one or more layers of nonwoven fibers substantially formed into the shape of a tube encircling the interior of the cartridge shell 103. An aerosol precursor composition can be retained in the reservoir 144. Liquid components, for example, can be sorptively retained by the reservoir 144 (i.e., when the reservoir 144 includes a fibrous material). The reservoir 144 can be in fluid connection with a liquid transport element 136. The liquid transport element 136 can transport the aerosol precursor composition stored in the reservoir 144 via capillary action to the heating element 134 that is in the form of a metal wire coil in this embodiment. As such, the heating element 134 is in a heating arrangement with the liquid transport element 136.

In use, when a user draws on the article 100, airflow is detected by the sensor 108, the heating element 134 is activated, and the components for the aerosol precursor composition are vaporized by the heating element 134. Drawing upon the mouthend of the article 100 causes ambient air to enter the air entry 118 and pass through the cavity 125 in the coupler 124 and the central opening in the projection 141 of the base 140. In the cartridge 104, the drawn air combines with the formed vapor to form an aerosol. The aerosol is whisked, aspirated, or otherwise drawn away from the heating element 134 and out the mouth opening 128 in the mouthend of the article 100.

In one or more embodiments, a mouthpiece 165 is provided according to the present disclosure, and the mouthpiece can be adapted to or configured to connect with the mouthend of the cartridge 104. As further described below, a flavor delivery article 290 may be included in the cartridge 104, such as proximate the mouthend of the cartridge. The flavor delivery article 290 may be positioned directly within the interior of the cartridge 104 so as to be at least partially surrounded by the cartridge shell 103. Alternatively or additionally, the flavor delivery article 290 can be positioned within the mouthpiece 165. Furthermore, in various embodiments, the mouthpiece 165 can be associated with, attached to, or otherwise connected with the mouthend of the cartridge 104. For example, the mouthpiece 165 can be adapted to or configured to be removably attached to the mouthend of the cartridge 104, such as through a screwthread connection, a magnetic connection, a press-fit (or friction-fit) connection, or the like. Moreover, the mouthpiece 165 can be adapted to or configured to be positioned over at least a portion of an exterior of the cartridge shell 103. Alternatively, the mouthpiece 165 can be adapted to or configured to be inserted into an opening formed in the mouthend of the cartridge shell 103.

An input element may be included with the aerosol delivery device. The input may be included to allow a user to control functions of the device and/or for output of information to a user. Any component or combination of components may be utilized as an input for controlling the function of the device. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference.

In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference in its entirety.

The aerosol delivery device can incorporate a sensor or detector for control of supply of electric power to the heat generation element when aerosol generation is desired (e.g., upon draw during use). As such, for example, there is provided a manner or method for turning off the power supply to the heat generation element when the aerosol delivery device is not be drawn upon during use, and for turning on the power supply to actuate or trigger the generation of heat by the heat generation element during draw. Additional representative types of sensing or detection mechanisms, structure and configuration thereof, components thereof, and general methods of operation thereof, are described in U.S. Pat. No. 5,261,424 to Sprinkel, Jr.; U.S.

Pat. No. 5,372,148 to McCafferty et al.; and PCT WO 2010/003480 to Flick; which are incorporated herein by reference.

The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. Pub. No. 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article illustrated in FIG. 1 or as otherwise described above may be included in an aerosol delivery device according to the present disclosure.

In one or more embodiments of the present disclosure, an aerosol delivery device may include a flavor delivery article. Said flavor delivery article, however, is understood as being a "stand-alone" element that may be provided in a variety of devices wherein it is desirable to entrain particles or droplets of a flavor liquid into a passing gaseous stream. For example, nebulizers, aerosolizers, medicament delivery devices, heat-not-burn (HNB) smoking articles, carbon tobacco heated products (CTHP), electrical tobacco heated products (ETHP), and the like all may benefit from incorporation of a flavor delivery article as described herein. Accordingly, it is understood that description of the flavor delivery article in combination with an aerosol delivery device is only to provide an example for complete disclosure of the invention, and the use of the flavor delivery article should be viewed as being limited to combination with aerosol delivery devices.

Figure 2:
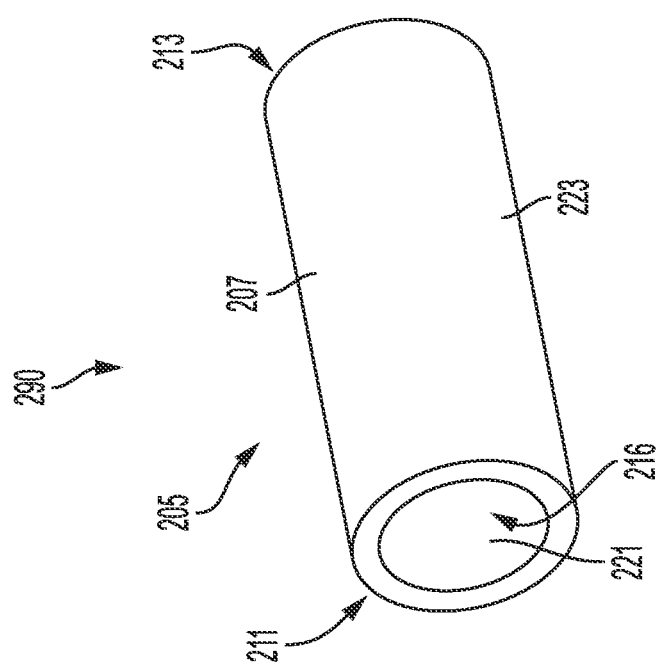
FIG. 2 illustrates a perspective view of an example embodiment of a hollow elongate unit of a flavor delivery article according to the present disclosure.

A flavor delivery article 290 as described herein can comprise a storage unit for holding or otherwise containing a flavor liquid. An example of such storage unit is illustrated in FIG. 2. As seen therein, the storage unit is illustrated as a hollow elongate unit 205 that is formed of a substantially continuous wall 207 extending between a first end 211 and a second end 213. The hollow elongate unit 205 can define an interior storage volume in the hollow space 216.

The hollow elongate unit 205, although illustrated as being substantially in the form of a tube or hollow cylinder, can take on a variety of shapes. For example, the hollow elongate unit can have a cross-sectional shape, such as a square, rectangle, oval, triangle polygon, or the like. Although illustrated as having a substantially continuous diameter across the length thereof, in some embodiments, the diameter of the hollow elongate unit 205 can vary along the length thereof. For example, the diameter may increase from the first end 211 to the second end 213 so that a diameter of the second end is greater than a diameter of the first end by about 25% to about 500%, about 50% to about 400%, or about 75% to about 250%. Alternatively, the diameter may decrease from the first end 211 to the second end 213 so that a diameter of the first end is greater than the diameter of the second end by about 25% to about 500%, about 50% to about 400%, or about 75% to about 250%. As such, the hollow elongate unit 205 may be substantially conical or frusto-conical in shape.

The hollow elongate unit 205 can vary in size depending upon the size of the further device in which it is to be included and the desired volume of flavor liquid to be stored therein. For example, the hollow elongate unit 205 can have a length of about 0.5 cm to about 5 cm, about 0.5 cm to about 3 cm, about 0.5 cm to about 2.5 cm, or about 0.5 cm to about 2 cm. The length of the hollow elongate unit 205 can be measured along a longitudinal axis thereof. The hollow elongate unit 205 further can have an average diameter or other dimension (e.g., width) that is measurable transverse to the longitudinal axis, and such other dimension can be about 0.2 cm to about 2 cm, about 0.3 cm to about 1.8 cm, or about 0.5 cm to about 1.5 cm. The substantially continuous wall 207 of the hollow elongate unit 205 can vary in thickness along the longitudinal axis of the unit. In some embodiments, the thickness of the substantially continuous wall 207 is preferably substantially uniform along the longitudinal axis of the unit. The substantially continuous wall 207, for example, can have an average thickness of about 0.05 mm to about 5 mm, about 0.1 mm to about 4 mm, or about 0.25 mm to about 3 mm. The interior storage volume of the hollow space 216 defined within the hollow elongate unit 205 can be about 2 cm$^3$ to about 500 cm$^3$, about 10 cm$^3$ to about 250 cm$^3$, about 25 cm$^3$ to about 200 cm$^3$, or about 50 cm$^3$ to about 100 cm$^3$.

The substantially continuous wall 207 of the hollow elongate unit 205 can be formed of a porous material that is configured such that flavor liquid stored within the hollow space 216 may diffuse through or wick through the interconnected pores. As such, the flavor liquid contacts an interior surface 221 of the substantially continuous wall 207 and passes through the interconnected pores to an exterior surface 223 of the substantially continuous wall 207. The substantially continuous wall 207 thus may be formed of a nanoporous, microporous, and/or macroporous material. In some embodiments, the substantially continuous wall 207 may be formed at least in part from one or more polymeric materials, such as polyethersulfone, polypropylene, polyethylene, polyester, nylon, cellulose nitrate, regenerated cellulose, cellulose acetate, and combinations thereof. For example, the substantially continuous wall 207 may be formed at least partially from fibers formed from any of the foregoing materials alone or in one or more combinations. Likewise, any one or more of the foregoing materials may be expressly excluded from use in one or more embodiments of the disclosure.

In some embodiments, the substantially continuous wall 207 may be formed at least in part from a ceramic material, such as alumina, silica, zirconia, or the like. If desired, a combination of materials may be utilized. Moreover, the substantially continuous wall 207 of the hollow elongate unit 205 may be formed from one or more layers (e.g., one layer, two layers, three layers, four layers, or more layers), and separate layers may be formed of different materials. When a plurality of layers is used, the layers can be prepared using coextrusion or other known techniques in the art. The substantially continuous wall 207 thus can be configured to absorb the flavor liquid that is stored within the hollow space 216 and transport the liquid flavor material via capillary action through the thickness of the substantially continuous wall. Once the liquid flavor material reaches the exterior surface of the substantially continuous wall 207, particles or droplets of the liquid flavor material can be entrained by a gaseous stream passing along the exterior surface thereof.

In some embodiments, the substantially continuous wall 207 (or one or more of a plurality of layers thereof) can be formed of a porous material having a graded porosity across a thickness of the substantially continuous wall. As used herein, a graded material or functionally graded material is understood to be a material wherein the composition, the microstructure, or both are locally varied so that a certain variation of the local material properties is achieved. Functionally graded materials are particularly useful for forming a substantially continuous wall as described herein in that they can be structurally engineered to allow for discrete or continual variations in the molecular modeling of the wall. This allows for preparation of coatings with varying capillary action across the thickness of the wall. The substantially continuous wall particularly can be defined as being functionally graded in that the average pore size can vary across the thickness of the wall. In some embodiments, the material(s) forming the substantially continuous wall are functionally graded such that the average pore size increases from an inner layer or section of the wall to an outer layer or section of the wall. As such, the wall can be functionally graded in average pore size from the inner layer or section of the wall to the outer layer or section of the wall such that the average pore size of the inner layer or section of the wall is smaller than the average pore size of the outer layer or section of the wall. In further embodiments, the material(s) forming the substantially continuous wall are functionally graded such that the average pore size decreases from an inner layer or section of the wall to an outer layer or section of the wall. As such, the wall can be functionally graded in average pore size from the inner layer or section of the wall to the outer layer or section of the wall such that the average pore size of the inner layer or section of the wall is greater than the average pore size of the outer layer or section of the wall.

Figure 3A:
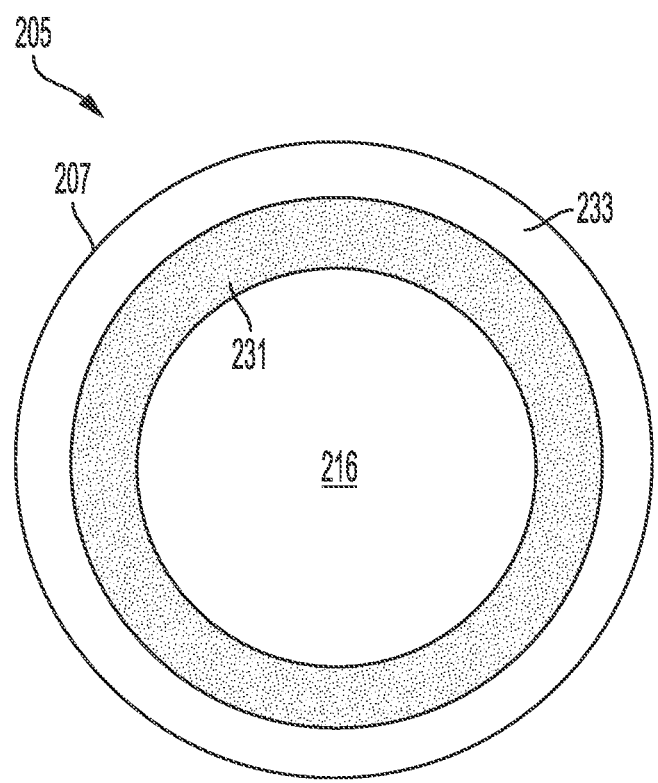
FIG. 3A illustrates a partial cross-sectional view of an example embodiment of a hollow elongate unit of a flavor delivery article according to the present disclosure.

An example embodiment of a hollow elongate unit 205 having a substantially continuous wall 207 that is functionally graded across a thickness thereof is shown in FIG. 3A. As seen therein, the substantially continuous wall 207 is formed of a first layer or inner layer 231 and a second layer or outer layer 233. The inner layer 231 is formed of a porous material having a first average pore size, and the outer layer 233 is formed of a porous material having a second average pore size. Relatively speaking, in some embodiments, the first average pore size can be smaller than the second average pore size, and the second average pore size can be greater than the first average pore size. In other embodiments, the first average pore size can be greater than the second average pore size, and the second average pore size can be smaller than the first average pore size. If desired, one or more intermediate layers may be included between the first (inner) layer 231 and the second (outer) layer 233, and the one or more intermediate layers can exhibit an average pore size that falls between the average pore size of the first (inner) layer and the second (outer) layer. As such, the substantially continuous wall 207 is functionally graded in that the average pore size changes across the thickness of the wall. Although the inner layer 231 and the outer layer 233 are illustrated as having substantially the same thickness, the relative thicknesses of the layers can be changed as desired to modify transfer of the vapor liquid across the full thickness of the substantially continuous wall 207. For example, in order to increase the amount of flavor liquid that is present at the exterior surface 223 of the substantially continuous wall 207 or to increase the rate of flow of the flavor liquid through the wall, the outer layer 233 may have a greater thickness than the inner layer 231. As such, the ratio of the thicknesses of the inner layer 231 to the outer layer can be about 0.1 to about 1, about 0.2 to about 1, about 0.5 to about 1, or about 0.75 to about 1. In other embodiments, the ratio of the thicknesses of the inner layer 231 to the outer layer can be about 1 to about 10, about 1 to about 8, or about 1 to about 5.

Figure 3B:
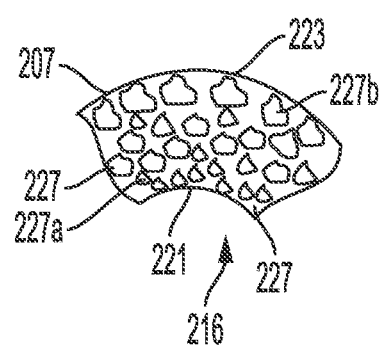
FIG. 3B illustrates a partial cross-sectional view of a portion of an example embodiment of a wall of a hollow elongate unit of a flavor delivery article according to the present disclosure.

FIG. 3B provides a further example embodiment of the substantially continuous wall 207 and illustrates an enlarged view of partial section of the wall. In the embodiment of FIG. 3B, the substantially continuous wall 207 is formed substantially or completely of a single layer of material; however, the single layer of material is graded across the thickness thereof. The substantially continuous wall 207 includes a plurality of pores 227. As illustrated, the substantially continuous wall 207 has relatively small pores 227*a* at or proximate the interior surface 221 of the wall and has relatively large pores 227*b* at or proximate the exterior surface 223 of the wall. In alternative embodiments, however, the relatively small pores can be at or proximate the exterior surface 223 of the wall, and the relatively large pores can be at or proximate the interior surface 221 of the wall. In some embodiments, the phrase "at the interior surface" can mean a volume that is adjacent the interior surface and that can extend outwardly a distance that is about 5% to about 45%, about 5% to about 35%, or about 5% to about 25% of the total thickness of the substantially continuous wall 207. Preferably, the defined volume extends around substantially the entire interior surface of the wall. Likewise, in some embodiments, the phrase "at the exterior surface" can mean a volume that is adjacent the exterior surface and that can extend inwardly a distance that is about 5% to about 45%, about 5% to about 35%, or about 5% to about 25% of the total thickness of the substantially continuous wall 207. Preferably, the defined volume extends around substantially the entire exterior surface of the wall.

The relatively small pores can have a first average size, and the relatively large pores can have a second average size. In further embodiments, pores having an intermediate average size that is between the first average size and the second average size can also be present. The intermediate average size can be referred to as a third average size. In one or more embodiments, the first average size for the relatively small pores can be about 10 nm to about 3 µm, about 100 nm to about 3 µm, about 250 nm to about 2.5 µm, or about 500 nm to about 2 µm. In further embodiments, the second average size for the relatively large pores can be about 0.5 µm to about 30 µm, about 1 µm to about 30 µm, about 2 µm to about 25 µm, or about 3 µm to about 20 µm. In some embodiments, the pores in approximately the inner half of the thickness of the substantially continuous wall 207 may have the first average pore size, and the pores in approximately the outer half of the thickness of the substantially continuous wall may have the second average pore size.

The range of gradation of the average pore size can be modified to determine how quickly flavor liquid from the hollow space 216 wicks through the thickness of the substantially continuous wall 207 to replenish liquid that is removed from the exterior surface 223 thereof. This can vary based upon the nature of the flavor liquid that is present in the hollow space 216 as well as the total amount of flavor liquid that is desired to be available for entrainment at a given time. Thus, the volume of the substantially continuous wall 207 that includes pores 227 having the second pore size can be reduced or increased as desired to reduce or increase, respectively, the amount of flavor liquid that is made available. For example, the pores 227 having the second average pore size can be present in approximately the outer 65%, the outer 45%, the outer 35%, the outer 25%, the outer 15%, or the outer 5% of the total thickness of the substantially continuous wall 207. Alternatively, the pores 227 having the first average pore size can be present in approximately the outer 65%, the outer 45%, the outer 35%, the outer 25%, the outer 15%, or the outer 5% of the total thickness of the substantially continuous wall 207.

In some embodiments, pore morphology may be graded across the thickness of the substantially continuous wall 207 so that wicking properties of a liquid through the substantially continuous wall may vary. For example, the pore morphology near the interior surface 221 of the substantially continuous wall 207 may be such that relatively rapid wicking occurs, and the pore morphology may change moving outward from the interior surface such that wicking rate decreases. As such, the pore morphology near the exterior surface 223 of the substantially continuous wall 207 may be such that relatively slower wicking occurs relative to the portion of the substantially continuous wall near the interior surface 221.

As noted above, a flavor liquid can be contained with the interior storage volume (i.e., the hollow space 216) of the hollow elongate unit 205. As such, in some embodiments an aerosol precursor composition held within the reservoir 144 (see FIG. 1) may comprise an unflavored aerosol precursor composition, though a flavored aerosol precursor composition (i.e., an aerosol precursor composition that includes one or more flavorants) is also contemplated. The flavor liquid then can include one or more flavorants, which may themselves be provided in the form of compositions with aerosol precursor components. As used herein, reference to a "flavorant" is intended to refer to compounds or components that can be present in a flavor liquid and that can be aerosolized and delivered to a user and which impart a sensory experience in terms of taste and/or aroma. Exemplary flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Exemplary plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. For other examples of flavoring materials that may be suitable for the products disclosed, see, for example, US Pat. Appl. Pub. Nos. 2002/0162562 to Williams; 2002/0162563 to Williams; 2003/0070687 to Atchley et al.; 2004/0020503 to Williams; 2005/0178398 to Breslin et al.; 2006/0191548 to Strickland et al.; 2007/0062549 to Holton, Jr, et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference. It should be noted that reference to a flavorant should not be limited to any single flavorant as described above, and may, in fact, represent a combination of one or more flavorants.

Figure 4:
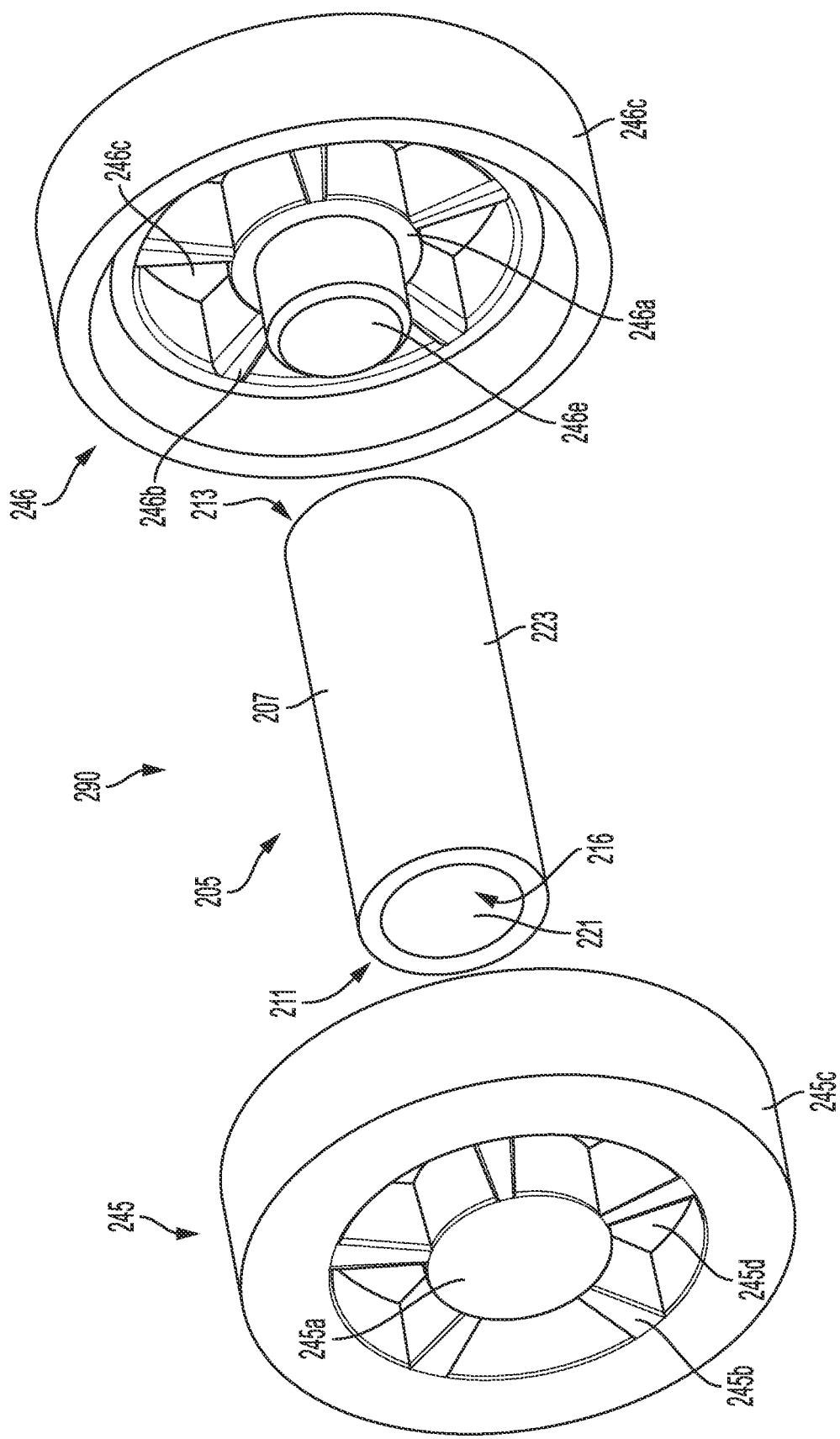
FIG. 4 illustrates an exploded view of an example embodiment of a flavor delivery article according to the present disclosure.
Figure 5:
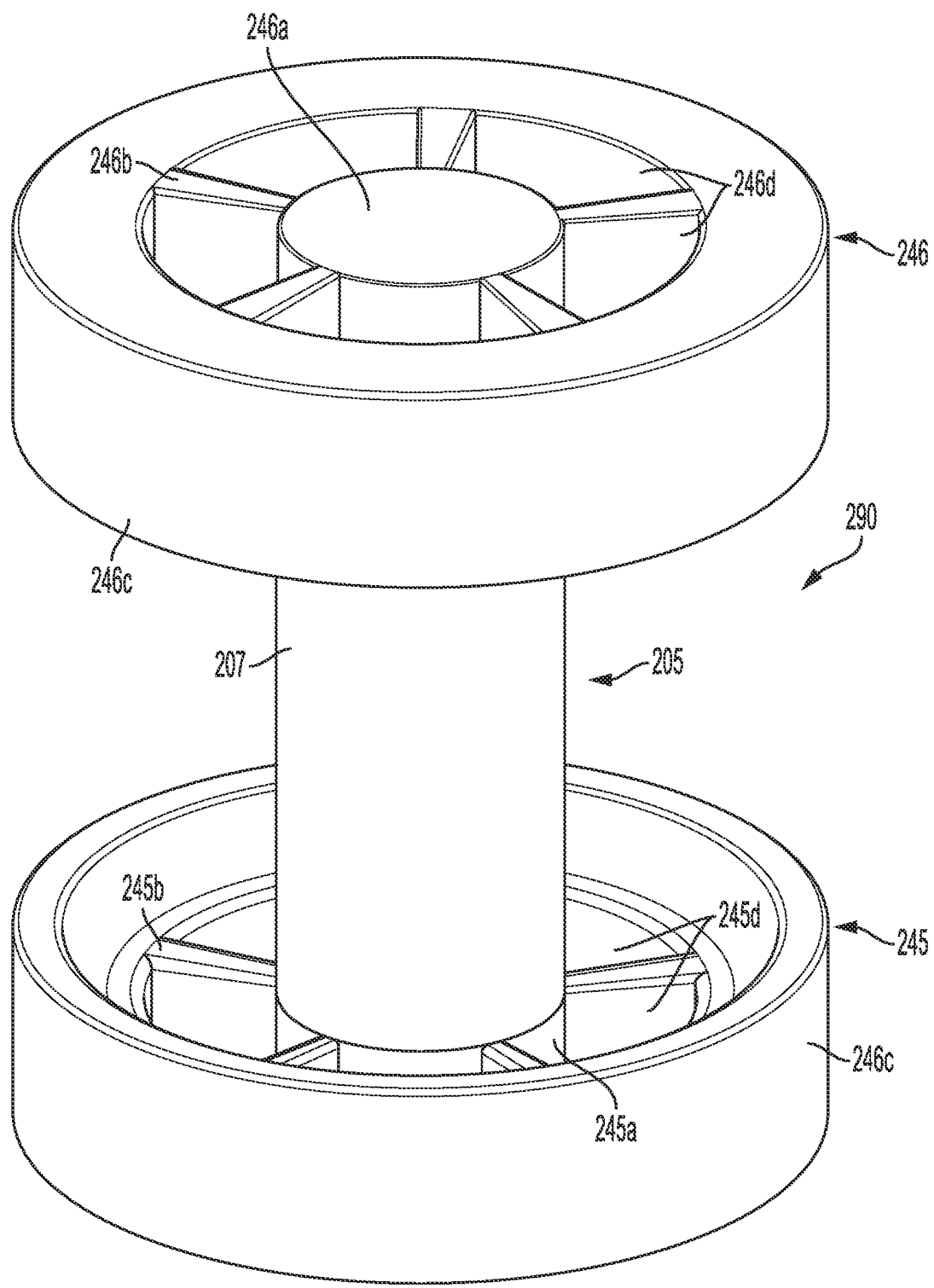
FIG. 5 illustrates a perspective view of an example embodiment of a flavor delivery article according to the present disclosure.

The hollow elongate unit 205 can be configured such that one or both of the first end 211 and the second end 213 is substantially open. This can facilitate filling of the hollow space 216 with the flavor liquid. The open ends, however, may also be configured for engaging one or more portions of one or more end units that can be useful for positioning the flavor delivery device within a portion of a further device, such as an aerosol delivery device. In particular, the flavor delivery article 290 further can comprise an end unit positioned on one or both of the first end 211 and the second end 213 of the hollow elongate unit 205. The end unit can be substantially a plug or cap (see element 371 in FIG. 9, for example) or can be substantially in the form of a frame. As illustrated in FIG. 4, a first end frame 245 is arranged for engagement of the first end 211 of the hollow elongate unit 205, and a second end frame 246 is arranged for engagement of the second end 213 of the hollow elongate unit. In the shown example embodiment, the first end frame 245 and the second end frame are substantially identical; however, the respective end frames may have differing constructions. In the example embodiment, both of the end frames (245, 246) have a hub and spoke configuration. In particular, the first end frame 245 includes a central hub 245a with a plurality of arms 245b (e.g., being configured as a spoke, with a substantially round cross-section, or being configured as vanes, with a substantially elongated cross-section) extending therefrom and connecting with an outer frame wall 245c. In the example embodiment of FIG. 4, the frames (245, 246) are substantially round, but it is understood that other shapes are encompassed. Moreover, a lesser or greater number of arms 245b may be used, and the dimensions of each element of the frames (245, 246) may vary independently. Similarly, the second end frame 246 includes a central hub 246a with a plurality of arms 246b (e.g., being configured as a spoke, with a substantially round cross-section, or being configured as vanes, with a substantially elongated cross-section) extending therefrom and connecting with an outer frame wall 246c. The second frame 246 further includes a shaft 246e extending from the hub 246a and configured for insertion into the hollow space 216 at the second end 213 of the hollow elongate unit 205. Other mechanisms for engagement of the frames (245, 246) with the first end 211 and second end 213 of the hollow elongate unit 205, however, are also encompassed. As illustrated, the engagement of the shaft 246 with the second end 213 of the hollow elongate unit 205 preferably is a sealing engagement so that flavor liquid stored in the hollow space 216 may not leak around the shaft. FIG. 5 shows the various elements of the flavor delivery article 290 combined with the two end frames (245, 246) engaging the respective first end 211 and second end 213 of the hollow elongate unit 205.

The central hubs (245a, 246a), the plurality of arms (245b, 246b), and the frame walls (245c, 246c) forming each of the frames define a plurality of openings (245d, 246d) therebetween, said openings being suitable for passage of a gaseous stream therethrough. The arrangement of the hubs, arms, and frame walls can thus define a lattice structure comprising a plurality of airflow passages therethrough. The lattice structure may be a wheel-type design as illustrated in the example embodiment of FIG. 4, but other lattice structures comprising a plurality of interconnecting sections so as to form an end frame are also encompassed.

The end frames (245, 246) can be formed of any suitable material that is non-reactive with the flavor liquid. In some embodiments, the end frames (245, 246) can be substantially non-porous or have a very low nanoporosity so that substantially none of the flavor liquid will significantly transfer therethrough. As non-limiting examples, the end frames (245, 246) can be made from inert materials, such as polymers and/or ceramics.

Figure 6:
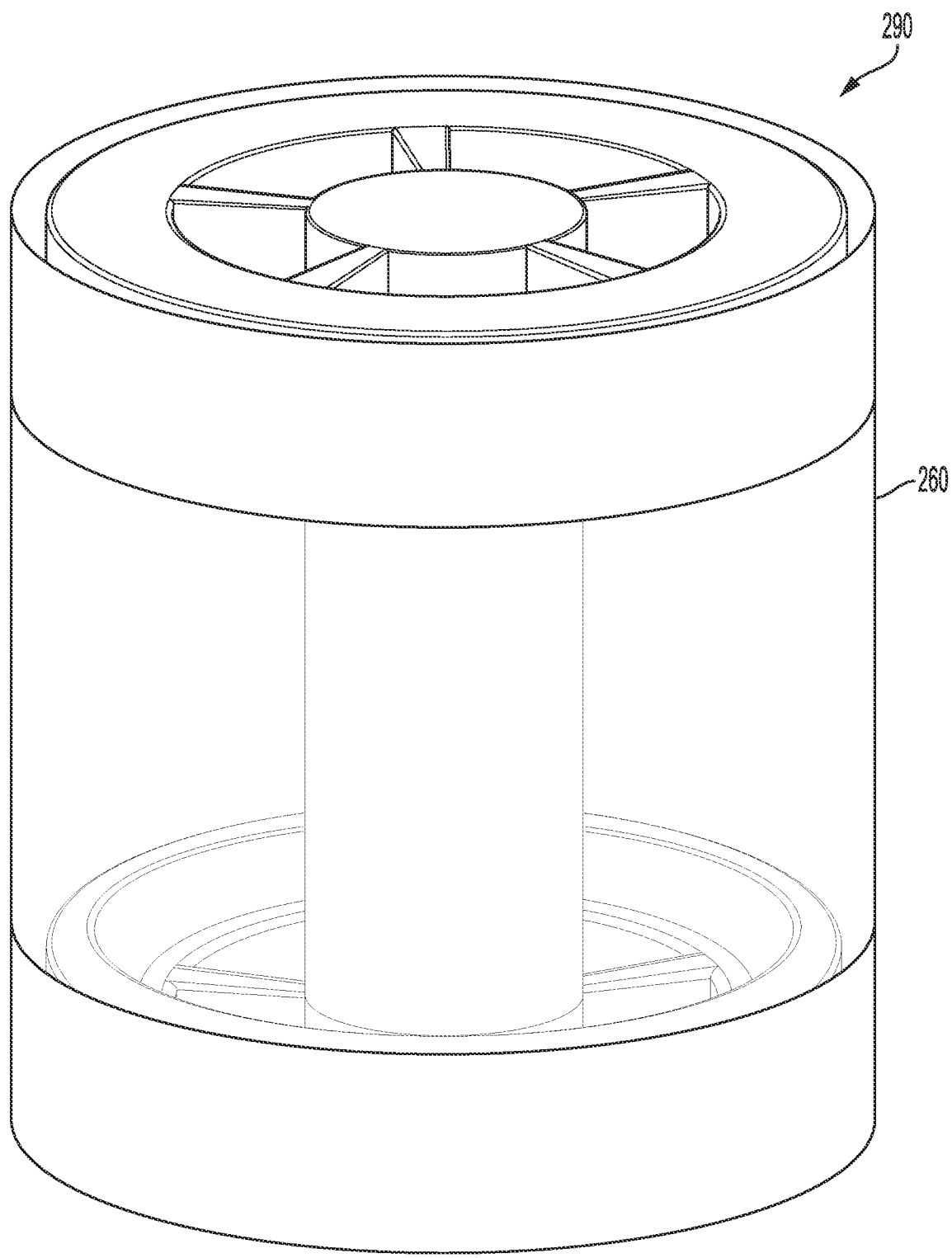
FIG. 6 illustrates a perspective view of an example embodiment of a flavor delivery article according to the present disclosure.

The flavor delivery article 290 can be provided substantially as shown in FIG. 5 (including being filled with a flavor liquid). In some embodiments, however, it can be desirable for the flavor delivery article 290 to further include an outer casing 260 as illustrated in FIG. 6. The outer casing 260 can extend from the first end frame 245 to the second end frame 246 and can be useful to provide the flavor delivery article 290 as a unit suitable for insertion into a variety of devices. In particular embodiments, the outer casing 260 can be useful to reduce or prevent loss of flavor liquid through evaporation across the exterior surface 223 of the substantially continuous wall 207 when the flavor delivery device (or a device into which the flavor delivery device is inserted) is not in use. Likewise, the outer casing 260 can be useful to retain any possible leakage from the further components of the flavor delivery unit. As non-limiting examples, the outer casing 260 can be formed from any suitable material, such as polymers including but not limited to polycarbonates, polyesters, polypropylene, polyethylene, or the like. As a further example, silicone or similar materials may be used.

The flavor delivery article 290 is beneficially useful for imparting a desired flavoring effect to a gaseous stream. As such, the flavor delivery article 290 can be combined with any type of device that is configured for providing a flow of a gaseous stream. This can include, in example embodiments, an aerosol delivery device such as illustrated in FIG. 1 or having different configurations of parts but intended to provide the same function of acting on an aerosol precursor liquid to form a vapor that can be entrained in a passing air stream and thus form an aerosol. For example, returning to FIG. 1, when the cartridge 104 is engaged with the power unit, a user drawing through the opening 128 at the mouthend of the cartridge will cause air to enter through the air entry 118. The air may flow through and/or around the reservoir 144 and entrain vapor that is formed by heating of aerosol precursor composition in the liquid transport element 136 by the heater 134 and thus form an aerosol that exits through the opening 128. There thus can be one or more airflow passages through the aerosol delivery device. As just described, the heater 134 can be positioned substantially within the airflow passage so that formed vapor is efficiently made available for entrainment in the air flowing through the cartridge 104.

In some embodiments, a flavor delivery article 290 as described herein can be positioned substantially within the airflow passage. For example, in FIG. 1, an open space is present between the heater 134 and the opening 128 at the mouthend of the cartridge 104. As such, a flavor delivery article 290 as described herein may be positioned in such an open space. In such configuration, the flavor delivery article 290 is positioned in an airflow passage downstream from the heater 134. In this manner, the aerosol drawn away from the heater 134 may pass across the flavor delivery article 290 for entrainment of the particles or droplets of the flavor liquid (including a flavorant as described herein). In further embodiments, a cartridge 104 may be configured to include additional space between the reservoir 144 and the base 140. In such embodiments, the air flowing through the cartridge will first pass across the flavor delivery article 290 prior to passing across or around the heater 134 to form the aerosol. As such, the air that is used to form the aerosol will already include particles or droplets of the flavor liquid entrained therein when the air mixes with vapor formed from the heater 134 to form the aerosol to be drawn through the opening 128. Accordingly, the flavor delivery article 290 can be positioned in the airflow passage upstream from the heater 134.

In some embodiments, the present disclosure specifically can provide a mouthpiece for an aerosol delivery device. The mouthpiece can include a flavor delivery device positioned therein and, as such, the flavor delivery mouthpiece that is so-formed can be adapted to or configured to be combined with another article, such as an aerosol delivery device.

Figure 7:
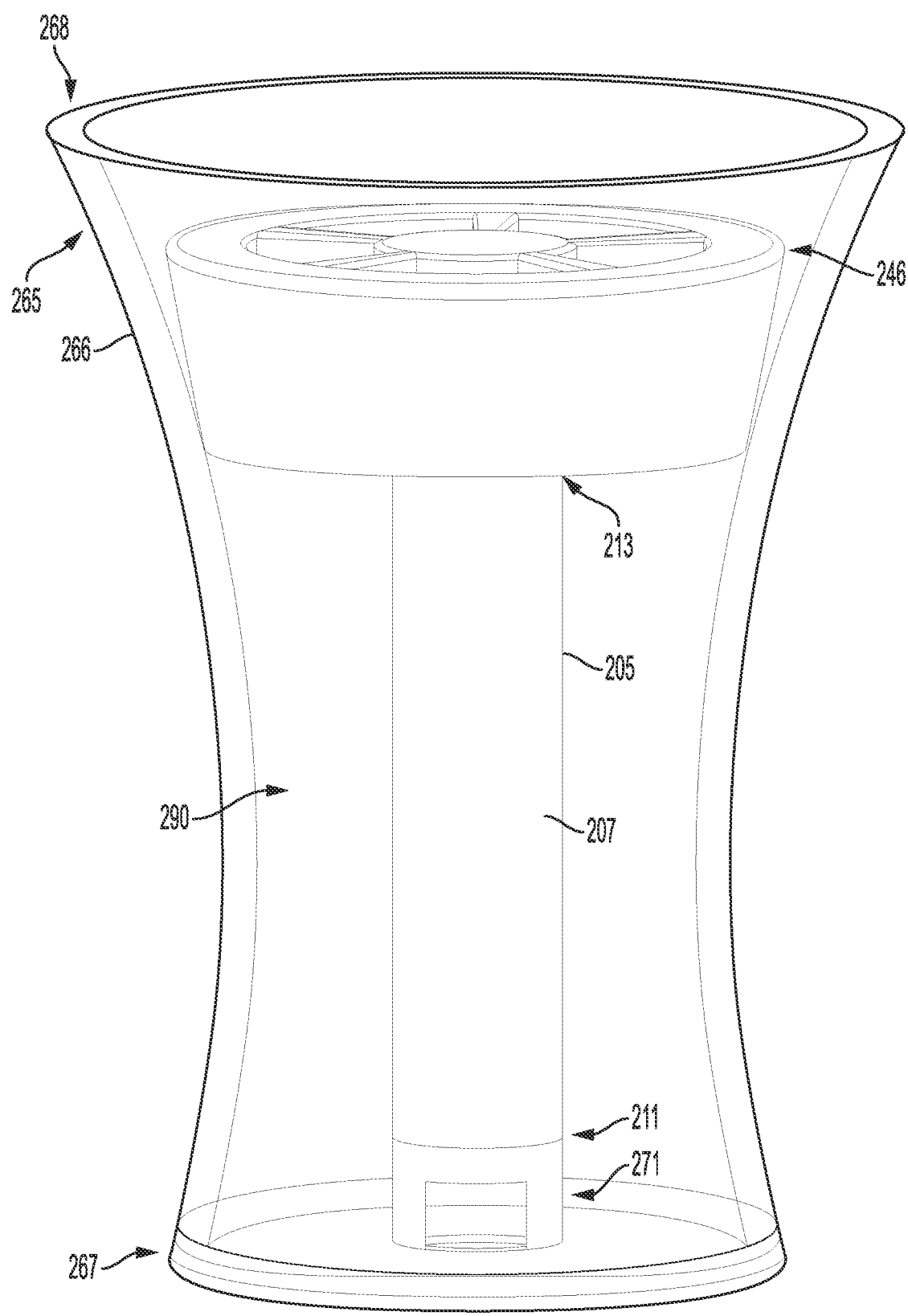
FIG. 7 illustrates a perspective view of an example embodiment of a flavor delivery article present within a mouthpiece of an aerosol delivery device according to the present disclosure.
Figure 8:
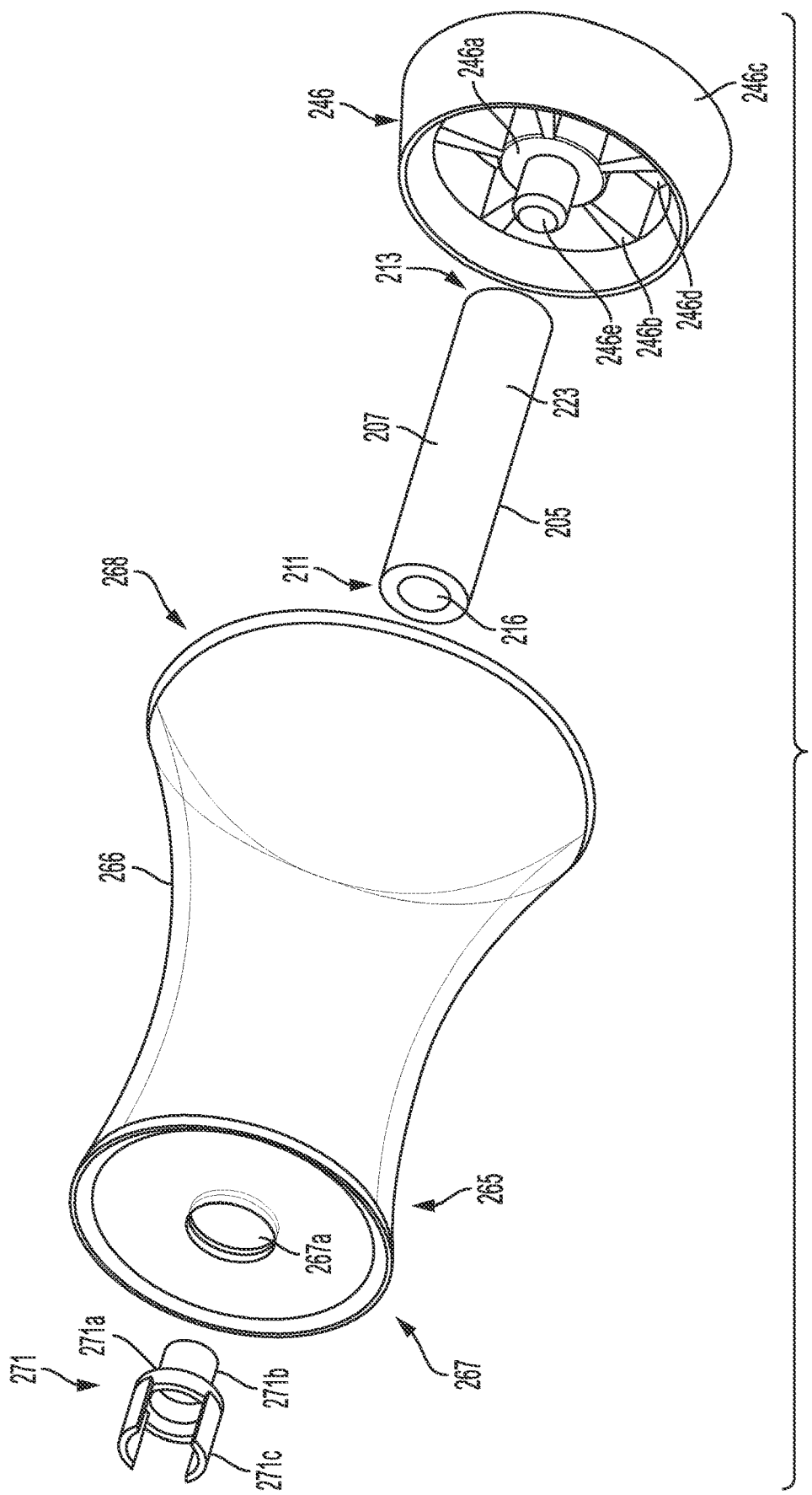
FIG. 8 illustrates an exploded view of an example embodiment of a flavor delivery article and a mouthpiece for an aerosol delivery device according to the present disclosure.

An example embodiment of a flavor delivery mouthpiece 265 is illustrated in FIG. 7. As seen therein, a mouthpiece 265 can be formed of a shell 266 having a first end 267 (or a connecting end configured for connection of the mouthpiece to a further device, such as the mouthend of a cartridge 104 as shown in FIG. 1) and a second end 268 (or a mouth end). The first end (or connecting end) 267 can be adapted to or configured to connect to an aerosol delivery device, such as through a screwthread connection, a magnetic connection, or a press-fit connection. The first end 267 of the mouthpiece 265 can include an opening 267a that can substantially align with the opening 128 in the mouthend of the cartridge 104 or with a similar opening in a further device to which the mouthpiece may be attached. The flavor delivery device 290 included in the mouthpiece 265 again includes a hollow elongate unit 205 that is formed of a substantially continuous wall 207 extending between a first end 211 and a second end 213. The hollow elongate unit 205 defines an interior storage volume for storage of the flavor liquid. A frame 246 is attached to the second end 213 of the hollow elongate unit 205, and the frame is substantially as otherwise described herein. At the first end 211 of the hollow elongate unit 205 is plug unit 271 comprising a floor member 271a, an extension 271b protruding therefrom and configured for engaging the first end 211 of the hollow elongate unit 205, and one or more curtains 271c extending downwardly from the floor member. The one or more curtains 271c extend only partially around the circumference of the floor member 271a and separate the floor member a distance away from the opening 267a in the first end 267 of the mouthpiece 265. In this manner, aerosol entering through the opening 267a in the mouthpiece 265 impinges on the bottom of the floor member 271a and spreads outwardly through the space(s) around the curtains. The aerosol then must pass longitudinally through the mouthpiece 265 passing across the exterior surface 223 of the substantially continuous wall 207 of the hollow elongate unit 205 where particles or droplets of the flavor liquid become entrained in the aerosol. The aerosol with the particles or droplets of the flavor liquid entrained therein then passes through the openings 246d between the arms 246b of the second frame 246 to exit the mouthpiece 265 through the second end 268 thereof. The combination of components is further illustrated in the exploded view of the example embodiment of the mouthpiece and flavor delivery article combination provided in FIG. 8.

Figure 9:
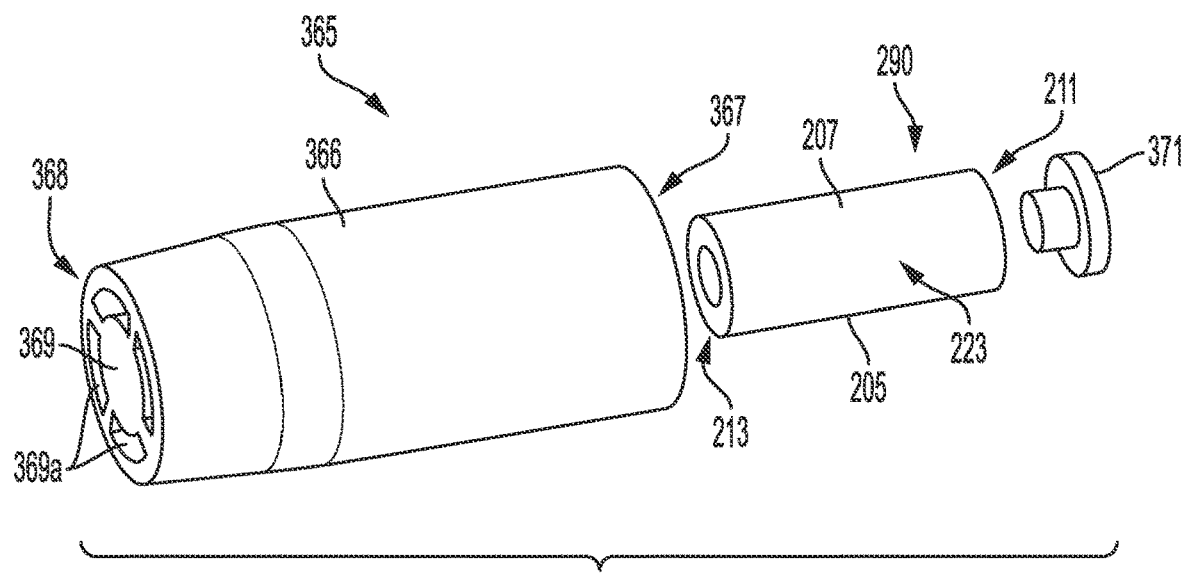
FIG. 9 illustrates an exploded view of an example embodiment of a flavor delivery article and a mouthpiece according to the present disclosure.

A further example embodiment of a flavor delivery mouthpiece 365 for combination with an aerosol delivery device or similar device is illustrated in FIG. 9. As seen therein, a mouthpiece 365 can be formed of a shell 366 having a first end 367 (or a connecting end configured for connection of the mouthpiece to a further device, such as the mouthend of a cartridge 104 as shown in FIG. 1) and a second end 368 (or a mouth end). The first end (or connecting end) 367 can be adapted to or configured to connect to an aerosol delivery device, such as through any suitable connection as otherwise noted herein.

The flavor delivery device 290 included in the mouthpiece 365 again includes a hollow elongate unit 205 that is formed of a substantially continuous wall 207 extending between a first end 211 and a second end 213. The hollow elongate unit 205 defines an interior storage volume for storage of the flavor liquid. At the first end 211 of the hollow elongate unit 205 is plug unit 371 is provided and is adapted to or configured to engage the first end 211 of the hollow elongate unit 205 and substantially prevent escape of flavor liquid therefrom. In this manner, aerosol entering at the first end 367 the mouthpiece 365 impinges on the plug unit 371 and spreads outwardly for passage around the hollow elongate unit 205. The aerosol then must pass longitudinally through the mouthpiece 365 passing across the exterior surface 223 of the substantially continuous wall 207 of the hollow elongate unit 205 where particles or droplets of the flavor liquid become entrained in the aerosol. The second end 368 of the shell 366 of the mouthpiece 365 includes an end wall 369 including a plurality of aerosol apertures 369a for passage of aerosol with entrained particles or droplets of the flavor liquid.

Figure 10:
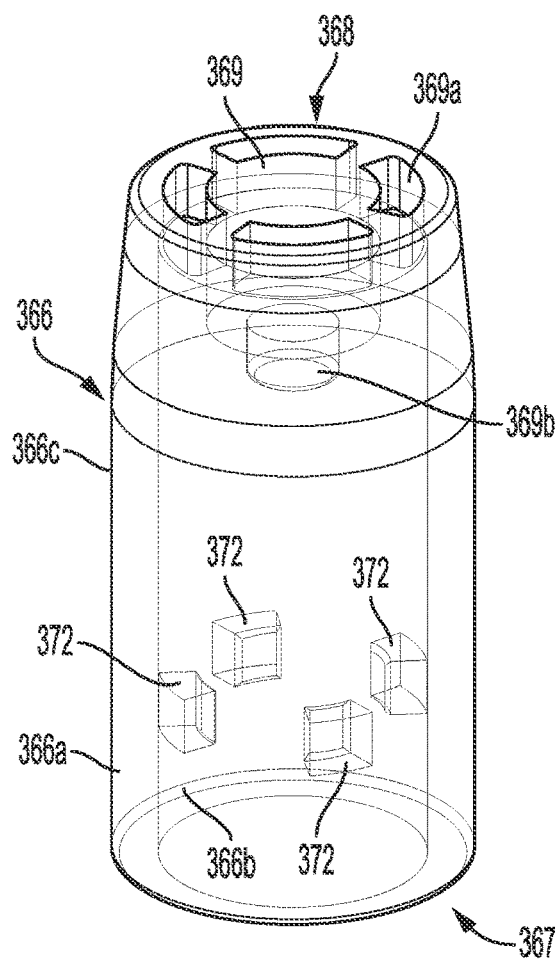
FIG. 10 illustrates a transparent view of a mouthpiece shell according to an example embodiment of the present disclosure.

The shell 366 of the mouthpiece 365 is further illustrated in FIG. 10 so as to reveal internal components thereof. As seen, the shell 366 is formed of a wall 366a with an interior surface 366b and an exterior surface 366c. The interior surface 366c includes a plurality of protrusions 372 that extend inwardly a distance from the interior surface of the shell 366. The number of protrusions 372 can vary as needed and are adapted to or configured to maintain a lateral position of the hollow elongate unit 205 within the shell 366. In an example embodiment, the protrusions 372 can be adapted to or configured to maintain a substantially centralized positioning of the hollow elongate unit 205 within the shell 366. The protrusions 372 are discontinuously spaced around a circumference of the interior surface 366b so as not to substantially impede aerosol flow through the interior of the shell 366 of the mouthpiece 365. The protrusions, as exemplified, are positioned proximate the first end 367 of the shell so as to be closer to the first end of the shell than to the second end 368 of the shell. Preferably, the protrusions in this embodiment can be positioned between about a midpoint of the longitudinal length of the shell 366 and the first end 367 of the shell.

The end wall 369 of the shell 366 further includes a mandrel 369b (or other element providing a like function) that projects inwardly into the interior of the shell and is sized and shaped to engage the opening in the second end 213 of the hollow elongate unit 205. The mandrel 369b and the protrusions 372 thus can work together to substantially stabilize the positioning of the flavor delivery device 290 within the shell 366 of the mouthpiece 365. The mandrel 369b is preferably substantially centrally positioned on the end wall 369 of the shell 366. The shell 366 of the mouthpiece 365 may be sized, for example, to substantially slide around an outer surface of a mouthend of an aerosol delivery device such that the interior surface 366b of the wall 366a of the shell 366 establishes a friction fit with the outer surface of the aerosol delivery device. In this manner, as a non-limiting example, the mouthpiece 365 may be removably connected to an aerosol delivery device or like device.

Figure 11:
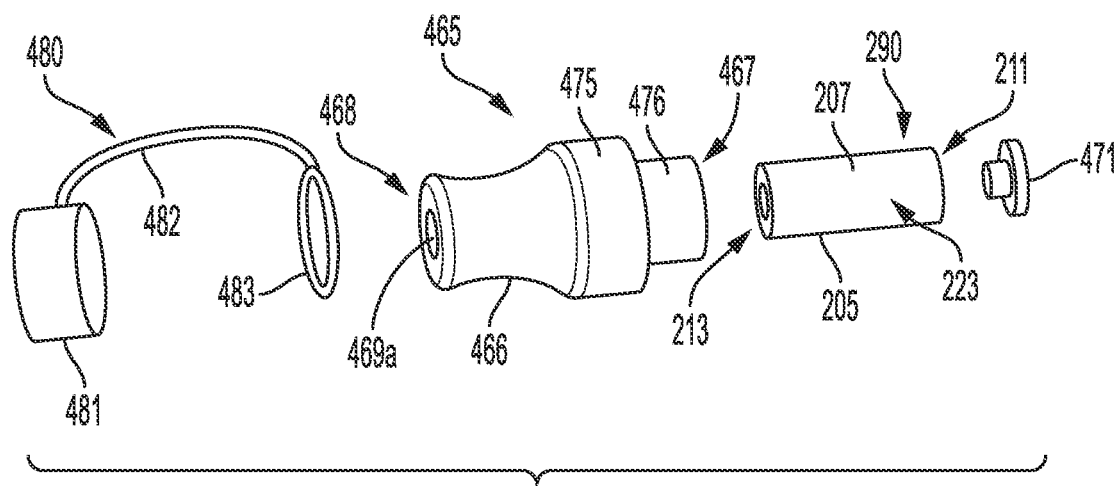
FIG. 11 illustrates an exploded view of an example embodiment of a flavor delivery article and a mouthpiece according to the present disclosure.

Another example embodiment of a flavor delivery mouthpiece 465 for combination with an aerosol delivery device or similar device is illustrated in FIG. 11. As seen therein, a mouthpiece 465 can be formed of a shell 466 having a first end 467 (or a connecting end configured for connection of the mouthpiece to a further device, such as the mouthend of a cartridge 104 as shown in FIG. 1) and a second end 468 (or a mouth end). The first end (or connecting end) 467 can be adapted to or configured to connect to an aerosol delivery device, such as through any suitable connection as otherwise noted herein. As illustrated, the first end 467 of the mouthpiece 465 extends toward the second end 468 a distance before widening at a flange 475. The area between the flange 475 and the first end 467 thus may form in insert 476 that is adapted to be or configured to be inserted into an opening in a mouthend of a cartridge. In this manner, as a non-limiting example, the mouthpiece 465 may be removably connected to an aerosol delivery device or like device.

The flavor delivery device 290 included in the mouthpiece 465 again includes a hollow elongate unit 205 that is formed of a substantially continuous wall 207 extending between a first end 211 and a second end 213. The hollow elongate unit 205 defines an interior storage volume for storage of the flavor liquid. At the first end 211 of the hollow elongate unit 205 is plug unit 471 is provided and is adapted to or configured to engage the first end 211 of the hollow elongate unit 205 and substantially prevent escape of flavor liquid therefrom. In this manner, aerosol entering at the first end 467 the mouthpiece 465 impinges on the plug unit 471 and spreads outwardly for passage around the hollow elongate unit 205. The aerosol then must pass longitudinally through the mouthpiece 465 passing across the exterior surface 223 of the substantially continuous wall 207 of the hollow elongate unit 205 where particles or droplets of the flavor liquid become entrained in the aerosol. The second end 468 of the shell 466 of the mouthpiece 465 includes an aperture 469a for passage of aerosol with entrained particles or droplets of the flavor liquid.

Figure 12:
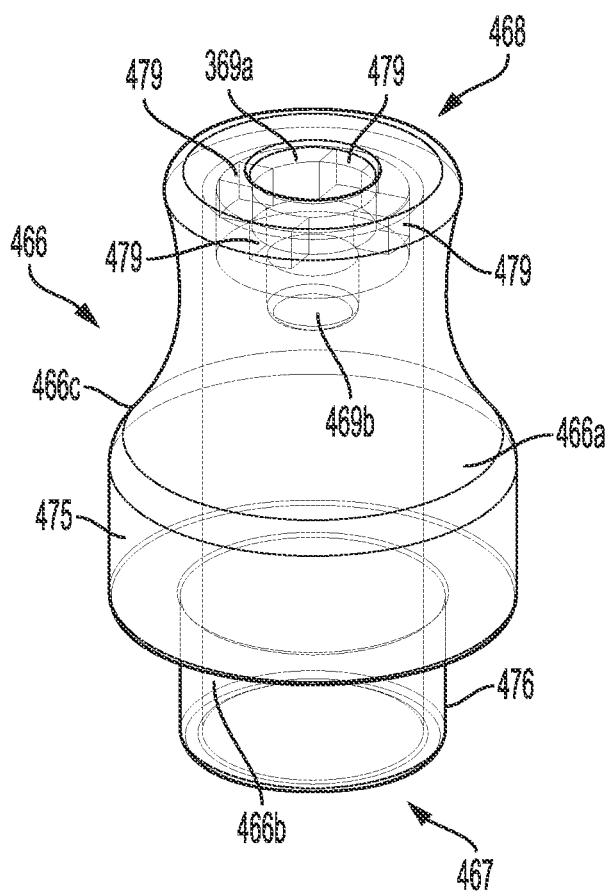
FIG. 12 illustrates a transparent view of a mouthpiece shell according to an example embodiment of the present disclosure.

The shell 466 of the mouthpiece 465 is further illustrated in FIG. 12 so as to reveal internal components thereof. As seen, the shell 466 is formed of a wall 466a with an interior surface 466b and an exterior surface 466c. The shell 466 further includes a mandrel 469b (or other element providing a like function) that projects inwardly into the interior of the shell and is sized and shaped to engage the opening in the second end 213 of the hollow elongate unit 205. The mandrel 369b is attached to the interior surface 466b of the shell 466 by a plurality of spacers 479 that maintain the mandrel 469b in a substantially centralized position and that also provide voids therebetween to allow aerosol passing around the substantially continuous wall 297 of the hollow elongate unit 205 to pass out of the shell 366 through the aperture 469a in the second end 468 of the shell.

Because the flavor liquid stored in the flavor delivery device is subject to becoming entrained in a passing airflow (and/or flow of aerosol), it may be possible for a certain content of the flavor liquid to spontaneously volatilize into surrounding, ambient air. Although this may represent only a de minimis amount of the flavor liquid present in the flavor delivery device, it can be desirable to provide the flavor delivery device and/or the mouthpiece with component(s) that are adapted to or configured to substantially prevent loss of flavor liquid. More particularly, this can substantially prevent or reduce scents or odors from escaping from the mouthpiece or another device including the flavor delivery device when undesired. Likewise, this can substantially prevent or reduce loss flavor liquid during times of non-use of the device which can undesirably shorten the useful lifetime of the flavor delivery device.

In one or more embodiments, a mouthpiece (265, 365, 465) according to the present disclosure can include one or more components that is adapted to or configured to substantially prevent any volatilized flavor liquid (or non-volatilized liquid that may otherwise seep or otherwise escape from the flavor delivery device) from exiting the mouthpiece. In one example embodiment, as seen in FIG. 11, a removably replaceable cover 480 can be provided. The removably replaceable cover 480 can include at least a cap 481 that can be sized and dimensioned to cover at least a portion of the second end 468 of the mouthpiece shell 466. In other embodiments, the cap 481 may be adapted to or configured to at least partially insert into the aperture 469a at the second end 468 of the mouthpiece shell 466. The cap thus can provide the functional aspects noted above and may also provide a hygienic function of substantially preventing contamination of the second end 468 of the mouthpiece shell 466 when the device is not in use. As illustrated, to aid in preventing loss of the cap 481, the removably replaceable cover 480 can optionally include a stem 482 connected at one end to the cap and at an opposing end to a loop 483 that can be sized to slide around the insert 476 of the mouthpiece shell 466; however, other configurations for attaching the cap 481 to the shell 466 of the mouthpiece 465 are also encompassed. The removably replaceable cover 480 may be formed of silicone or a flexible polymeric material.

Figure 13:
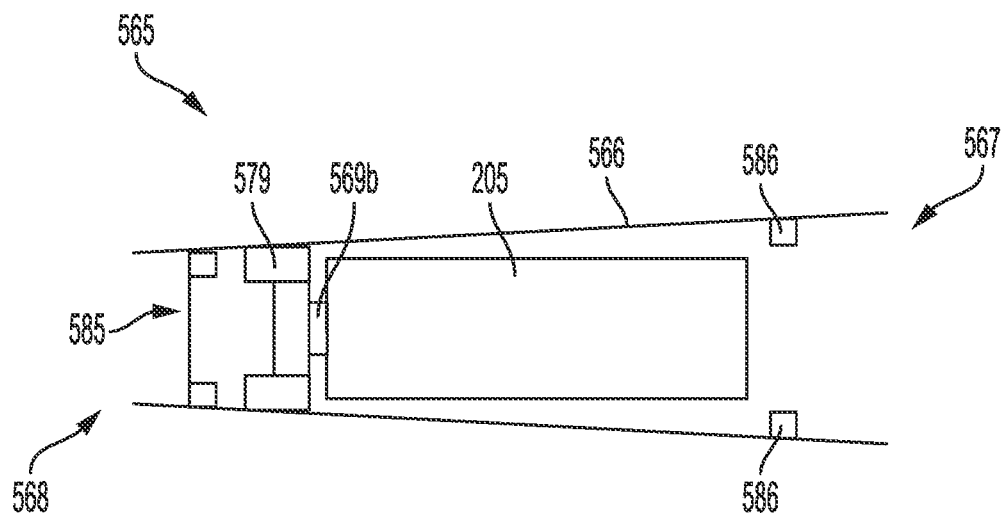
FIG. 13 illustrates a partial cross-sectional view of a mouthpiece including a flavor delivery article according an example embodiment of the present disclosure.

In some embodiments, one or more valves may be utilized to substantially prevent any volatilized flavor liquid from exiting the mouthpiece. As illustrated in FIG. 13, a mouthpiece 565 includes shell 566 having a first end (or attaching end) 567 and a second end (or mouth end) 568. Inside the shell 566, spacers 579 are utilized to attach a mandrel 569b to the shell, and a hollow elongate unit 205 as otherwise described herein is attached to the mandrel. The mouthpiece 565 includes a valve 585 (e.g., a one-way valve or check valve) that is illustrated in a closed position but that it adapted to or configured to open when air flows through the mouthpiece from the first end 567 of the shell 566 to the second end 568 of the shell. The valve 568 can be biased in the closed position with an appropriate biasing mechanism, such as a spring or the like, which can be included in the valve or be a separate element. As shown in FIG. 13, the mouthpiece 565 can include one or a plurality of projections 586 located proximate the first end 567 of the shell 566 to assist in providing a friction fit of the mouthpiece over a mouthend of an aerosol delivery device. The projections can be adapted to or configured to substantially prevent pushing the mouthpiece too far onto the end of an aerosol delivery device so that the hollow elongate unit 205 may become damaged or an insufficient amount of air and/or aerosol will flow out of the mouthend of the aerosol delivery device and through the mouthpiece.

In another aspect, the disclosure can be directed to kits that provide a variety of components as described herein. For example, a kit can comprise a control body with one or more cartridges. A kit further can comprise a control body with one or more charging components. A kit further can comprise a control body with one or more batteries. A kit further can comprise a control body with one or more cartridges and one or more charging components and/or one or more batteries. In further embodiments, a kit can comprise a plurality of cartridges. A kit further can comprise a plurality of cartridges and one or more batteries and/or one or more charging components. The kits further can include a case (or other packaging, carrying, or storage component) that accommodates one or more of the further kit components. The case could be a reusable hard or soft container. Further, the case could be simply a box or other packaging structure. In still further embodiments, the disclosed kits can comprise a mouthpiece as described herein and one or more flavor delivery article as described herein. Further, the kits can comprise a plurality of mouthpieces packaged together for disposable use with an aerosol delivery device. Still further, kits can include one or more mouthpieces and one or more flavor delivery articles and/or one or more cartridges as described herein.

The foregoing description of use of the device can be applied to the various implementations described herein through minor modifications, which can be apparent to the person of skill in the art in light of the further disclosure provided herein. The above description of use, however, is not intended to limit the use of the article but is provided to comply with all necessary requirements of disclosure of the present disclosure.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A flavor delivery article comprising:
   an elongate unit formed of a wall extending between a first end and a second end, the elongate unit having a hollow interior storage space so that the elongate unit is in the form of a tube or hollow cylinder, and the wall being formed of a porous material with interconnected pores having a graded porosity across a thickness of the wall; and
   a flavor liquid contained within the hollow interior storage space of the elongate unit and configured to diffuse through or wick through the interconnected pores of the wall from an interior surface of the wall to an exterior surface of the wall.

2. The flavor delivery article of claim 1, wherein the porous material forming the wall of the elongate unit is a polymeric material.

3. The flavor delivery article of claim 2, wherein the polymeric material is selected from the group consisting of polyethersulfone, polypropylene, polyethylene, polyester, nylon, cellulose nitrate, regenerated cellulose, cellulose acetate, and combinations thereof.

4. The flavor delivery article of claim 1, wherein the porous material forming the wall of the elongate unit is a ceramic material.

5. The flavor delivery article of claim 1, wherein the graded porosity is configured such that an average size of the interconnected pores in the wall of the elongate unit increases across the thickness of the wall from the interior surface to the exterior surface of the wall.

6. The flavor delivery article of claim 5, wherein the interconnected pores in the wall of the elongate unit have a first average size at one of the interior surface and the exterior surface of about 10 nm to about 3 µm.

7. The flavor delivery article of claim 5, wherein the interconnected pores in the wall of the elongate unit have a second average size at an other of the interior surface and the exterior surface of about 0.5 µm to about 30 µm.

8. The flavor delivery article of claim 1, wherein one or both of the first end and the second end of the elongate unit is open.

9. The flavor delivery article of claim 1, further comprising an end unit engaging one or both of the first end and the second end of the elongate unit.

10. The flavor delivery article of claim 9, wherein the end unit is a lattice structure comprising a plurality of airflow passages therethrough.

11. The flavor delivery article of claim 9, wherein the flavor delivery article further comprises an outer casing.

12. A flavor delivery mouthpiece comprising:
    a flavor delivery article according to claim 1 positioned within a mouthpiece shell that includes a first end and an opposing, second end, the second end including one or more apertures adapted for passage of air therethrough, wherein the flavor delivery article positioned within the mouthpiece shell is spaced apart from an interior surface of the mouthpiece shell so as to allow passage of the air through the mouthpiece shell between the flavor delivery article and the interior surface of the mouthpiece shell.

13. The flavor delivery mouthpiece of claim 12, wherein the mouthpiece shell comprises one or more protrusions extending inwardly from the interior surface of the mouthpiece shell.

14. The flavor delivery mouthpiece of claim 13, wherein the one or more protrusions are adapted to contact with flavor delivery article and substantially maintain a lateral position of the flavor delivery article within the mouthpiece shell.

15. The flavor delivery mouthpiece of claim 12, further comprising a mandrel positioned within the mouthpiece shell proximate to the second end thereof, the mandrel being adapted to engage one of the first end and the second end of the hollow elongate unit of the flavor delivery article.

16. The flavor delivery mouthpiece of claim 12, further comprising a removably replaceable cover adapted to engage the second end of the mouthpiece shell.

17. A cartridge for an aerosol delivery device, the cartridge comprising:
    a cartridge housing having a mouthend;
    a reservoir including an aerosol precursor composition;
    a heater adapted to vaporize the aerosol precursor composition; and
    a flavor delivery mouthpiece according to claim 12 engaged with the cartridge such that the first end of the mouthpiece shell is attached to the mouthend of the cartridge housing.

18. The cartridge of claim 17, further comprising a liquid transport element configured for transport of the aerosol precursor composition between a reservoir and the heater.

19. The cartridge of claim 17, wherein the reservoir includes a fibrous material.

20. The cartridge of claim 17, wherein the reservoir is a tank.

21. An aerosol delivery device comprising:
   a power unit housing including a power source and a controller; and
   a cartridge according to claim 17.

22. A cartridge for an aerosol delivery device, the cartridge comprising:
   a cartridge housing having a mouthend;
   a reservoir including an aerosol precursor composition;
   a heater adapted to vaporize the aerosol precursor composition; and
   a flavor delivery article comprising:
      an elongate unit formed of a wall extending between a first end and a second end, the elongate unit having a hollow interior storage space so the elongate unit is in the form of a tube or hollow cylinder, and the wall being formed of a porous material with interconnected pores having a graded porosity across a thickness of the wall; and
      a flavor liquid contained within the hollow interior storage space of the elongate unit and configured to diffuse through or wick through the interconnected pores of the wall from an interior surface of the wall to an exterior surface of the wall.

23. The cartridge of claim 22, further comprising an air entry and an airflow passage through the cartridge.

24. The cartridge of claim 23, wherein the heater and the flavor delivery article are both positioned substantially within the airflow passage.

25. The cartridge of claim 23, wherein the flavor delivery article is positioned in the airflow passage upstream from the heater.

26. The cartridge of claim 23, wherein the flavor delivery article is positioned in the airflow passage downstream from the heater.

27. The cartridge of claim 22, wherein the flavor delivery article is positioned in a mouthpiece attached to the mouthend of the cartridge housing.

* * * * *